United States Patent [19]

Iwasaki

[11] Plant 4,251

[45] May 16, 1978

[54] CHRYSANTHEMUM PLANT NAMED IMPERIAL WHITE

[76] Inventor: Satoru Iwasaki, 2519 Pulgas Ave., East Palo Alto, Calif. 94303

[21] Appl. No.: 765,107

[22] Filed: Feb. 2, 1977

[51] Int. Cl.[2] ..... A01H 5/00

[52] U.S. Cl. ..... Plt./77

[58] Field of Search ..... Plt./77

*Primary Examiner*—Robert E. Bagwill

*Attorney, Agent, or Firm*—Chas. W. Rummler

[57] ABSTRACT

A new variety of chrysanthemum plant originating as a sport of the unpatented cultivar Albatross and distinguished by its much larger flower size and more incurved form, its longer form retention, the increased diameter and length of its stems, and the larger and more luxurious appearance of its foliage.

5 Drawing Figures

BACKGROUND OF THE NEW PLANT

My new chrysanthemum was discovered by me at East Palo Alto, Calif., as a sport of a plant of the variety Albatross being grown in my greenhouse for the commercial market. The clear white color and large size of the bloom and growth of this sport prompted me to reproduce it by means of cuttings from the flowering stem in the hope that I had found a new plant of valuable commercial merit and propagation of this plant through successive generations by vegetative cuttings, at my nursery at East Palo Alto, Calif., has demonstrated that its distinctive features hold true from generation to generation and appear to be firmly fixed.

DESCRIPTION OF THE DRAWINGS

This new chrysanthemum variety is illustrated by the accompanying photographic drawings, one sheet of which shows, in one view, the form and coloration of a typical bloom of the new variety and in another view, a side-by-side comparison of the blossom of the new plant with the blossom of its parent, the latter being the smaller flower at the left of this view. The second sheet of the drawings shows the configuration of typical leaves of this new plant by photo-mechanical reproduction of machine made prints of freshly cut specimens.

DESCRIPTION OF THE NEW PLANT

The following is a detailed description of my new variety of chrysanthemum plant with color designations according to the R.H.S. Colour Chart produced by The Royal Horticultural Society, at London, England, in collaboration with The British Colour Counsel. The colors stated are as observed during October flowering.

THE PLANT

Origin: Sport.
Parentage: Albatross (unpatented).
Classification:
*Botanic.*—*Chrysanthemum morifolium.*
*Commercial.*—Standard, incurved.
Form: Herbaceous bush.
Height: 2 to 4 feet.
Growth: Terminal. Sturdy and upright with very good strength and vigor.
Branching: Normal under natural conditions.
Foliage: Abundant, with 5 to 7 leaves per 6 inches of stem.

*Leaf size.*—4¼ to 6¼ inches long and 2¼ to 3⅜ inches wide.
*Leaf shape.*—Lobed — lanceolate and slightly serrated.
*Surface aspect.*—Shiny.
*Venation.*—Pinnate.
*Color.*—Upper side — 137A. Under side — 146A.
*Petioles.*—¾ to 1 inch long.

Recommended only for greenhouse culture.

THE BUD

Form: Semispherical.
Size:
*Diameter.*—⅝ to ⅞ inch.
*Depth.*—5/16 to 7/16 inch.
Opening rate: The bud opens slowly.
Color:
*When phyllaries first divide.*—144B.
*When florets begin to unfurl.*—5B.
Phyllaries: Spear shaped.
*Color.*—Inside — 144A. Outside — 147B.
*Surface appearance.*—Pubescent.
Peduncle: Strong and erect.
*Length.*—1½ to 3 inches.
*Surface appearance.*—Pubescent.

THE FLOWER

Response: 9 weeks.
Recommended flowering: March 1 to December 15.
Natural season flowering: Last week of October.
Blooms: Flower type — Standard incurved.
*Shape.*—Flat when flower first opens, becoming more globular as flower matures.
*Size.*—Very large. Diameter 5½ to 7 inches. Depth — 3½ to 4 inches.
*Borne.*—One head of many florets borne on a single receptacle.
*Florets.*—340 to 390 in number. Form: Linear with an acute apex. Color: 155B to 155D for both sides of all florets. Firmness: Medium. Appearance: Shiny.
*Discoloration.*—None.
*Peduncle.*—Sturdy and upright. Length: 1½ to 3 inches. Color: 147B.
Persistence: Florets hang on and dry.
Fragrance: Typical chrysanthemum.
Lasting quality:

*On plant.*—3 weeks.

*As cut flower.*—12 to 16 days.

REPRODUCTIVE ORGANS

Stamens:

*Filaments.*—Connate by their anthers to form a cylinder about the style. Length — ⅛ inch. Color — Yellow.

*Anthers.*—Length — 1/16 inch.

*Pollen.*—Color — Yellow.

Pistils: Number — one for each ray floret.

*Style.*—Length — ¼ to ⅜ inch.

*Stigmas.*—Color — Yellow.

Ovaries: Inferior — bicarpellate.

This new chrysanthemum has substantially the same growth and blooming habit as its parent and its floral coloration is the same. Its distinguishing differences, however, reside in the considerably larger size of its blooms and foliage and in this regard the material differences of the new plant from its parent are shown by the following table.

| | Imperial White | Albatross |
|---|---|---|
| Blossom: | | |
| Form: | Incurved, more than Albatross | Incurved |
| Size: | 5-1/2 to 7 inches | 4 to 5-1/4 inches |
| Petals: | | |
| Length: | 2-3/4 to 3-1/4 inches | 2-1/4 to 2-3/4 inches |
| Width: | 5/8 to 3/4 inch | 9/16 to 11/16 inch |
| Form Retention Under High Temperature: | Minimal reflexing | Considerable reflexing |
| Foliage: | | |
| Leaf Size: | | |
| Length: | 4-1/4 to 6-3/4 inches | 3-7/8 to 5-1/4 inches |
| Width: | 2-1/4 to 3-5/8 inches | 1-3/4 to 2-1/4 inches |
| Texture: | Very coarse | Coarse |
| Plant: | | |
| Height: | 2 to 4 feet | 20% to 25% less than Imperial White |
| Stem Diameter: | 5/16 to 7/16 inch | 1/4 to 3/8 inch |

I claim:

1. A new and distinct cultivar of chrysanthemum plant, substantially as herein shown and described, characterized by the larger size of its blooms and foliage, when compared with its parent plant, and the greater height and size of its flowering stems.

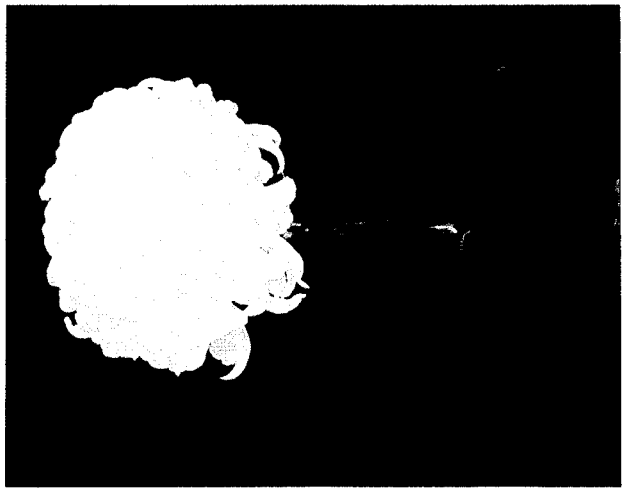
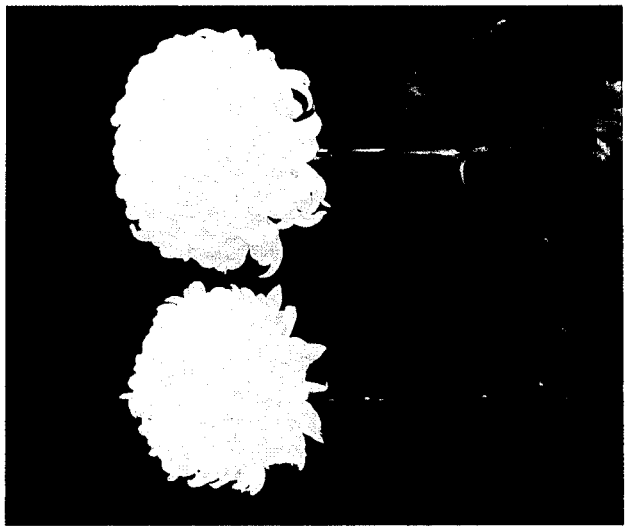

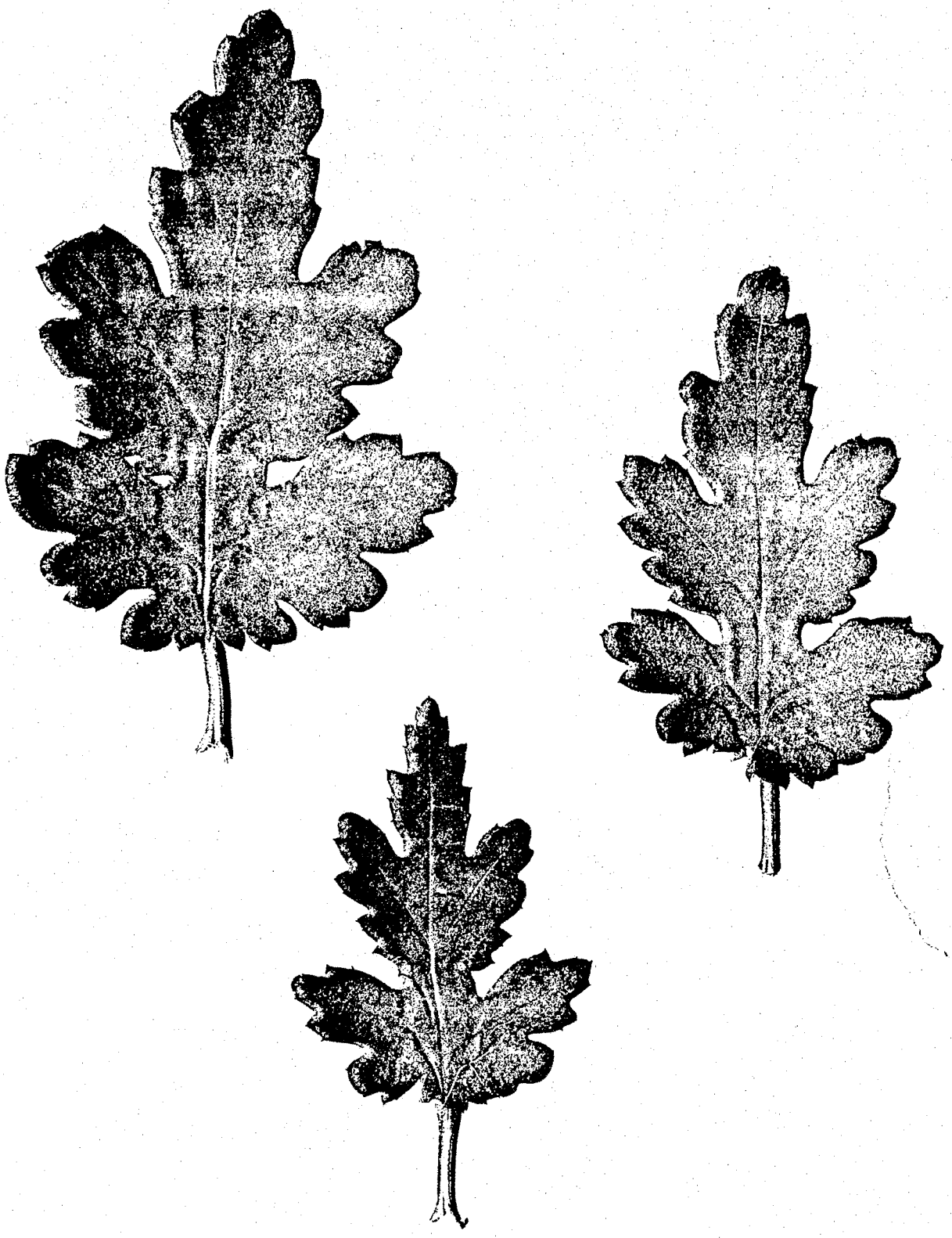

* * * * *